(12) United States Patent
Teramoto

(10) Patent No.: US 11,078,926 B2
(45) Date of Patent: Aug. 3, 2021

(54) BLOWER

(71) Applicant: Nidec Corporation, Kyoto (JP)

(72) Inventor: Takuya Teramoto, Kyoto (JP)

(73) Assignee: NIDEC CORPORATION, Kyoto (JP)

( * ) Notice: Subject to any disclaimer, the term of this patent is extended or adjusted under 35 U.S.C. 154(b) by 500 days.

(21) Appl. No.: 16/132,525

(22) Filed: Sep. 17, 2018

(65) Prior Publication Data

US 2019/0017517 A1   Jan. 17, 2019

Related U.S. Application Data

(63) Continuation of application No. 14/842,902, filed on Sep. 2, 2015, now Pat. No. 10,125,791.

(30) Foreign Application Priority Data

Nov. 17, 2014  (JP) .................................. 2014-232320
Apr. 28, 2015  (JP) .................................. 2015-091579

(51) Int. Cl.
| | | |
|---|---|---|
| *A61M 16/00* | (2006.01) | |
| *F04D 29/58* | (2006.01) | |
| *H02K 1/18* | (2006.01) | |
| *F04D 17/16* | (2006.01) | |
| *F04D 25/06* | (2006.01) | |
| *F04D 29/056* | (2006.01) | |
| *F04D 29/28* | (2006.01) | |
| *F04D 29/42* | (2006.01) | |

(Continued)

(52) U.S. Cl.
CPC ....... *F04D 29/582* (2013.01); *A61M 16/0066* (2013.01); *F04D 17/16* (2013.01); *F04D 25/06* (2013.01); *F04D 29/056* (2013.01);

*F04D 29/281* (2013.01); *F04D 29/4233* (2013.01); *F04D 29/668* (2013.01); *H02K 1/185* (2013.01); *H02K 9/22* (2013.01)

(58) Field of Classification Search
CPC ........ F04D 29/582; F04D 17/16; F04D 25/06; F04D 29/056; F04D 29/281; F04D 29/4233; F04D 29/668; A61M 16/0066; H02K 1/185; H02K 9/22
USPC .................................................... 128/204.18
See application file for complete search history.

(56) References Cited

U.S. PATENT DOCUMENTS

2012/0121426 A1   5/2012   Kitamura

FOREIGN PATENT DOCUMENTS

JP   2013-255303 A   12/2013

OTHER PUBLICATIONS

Teramoto, "Blower", U.S. Appl. No. 14/842,902, filed Sep. 2, 2015.

*Primary Examiner* — Andrew S Lo
(74) *Attorney, Agent, or Firm* — Keating & Bennett

(57) ABSTRACT

A centrifugal blower includes a stator housing. The stator housing includes a radial contact surface which makes contact with a casing in a radial direction, a circumferential contact surface which makes contact with the casing in a circumferential direction, and an axial contact surface which makes contact with the casing in an axial direction. With such configuration, it is possible to reduce the vibration of the blower by increasing a contact area between the casing and the stator housing. Further, the stator housing includes a heat dissipating surface. As a result, it is possible to efficiently dissipate the heat, which is generated from the stator, from the heat dissipating surface of the stator housing to the gas existing within the wind tunnel.

11 Claims, 10 Drawing Sheets

(51) Int. Cl.
*F04D 29/66* (2006.01)
*H02K 9/22* (2006.01)

BLOWER

BACKGROUND OF THE INVENTION

1. Field of the Invention

The present invention relates to a centrifugal blower.

2. Description of the Related Art

In the related art, there is known a centrifugal blower mounted to a device having a blowing function, such as an artificial respirator, a cleaner, a cooling fan or the like. In the centrifugal blower, an impeller disposed within a casing is rotated by the power of a motor, thereby sucking a gas from a suction port of the casing and discharging the gas from an exhaust port of the casing. Centrifugal blowers of the related art are disclosed in, e.g., U.S. Pat. Nos. 6,960,854, 8,638,014 and U.S. Patent Application Publication No. 2012/0199129.

When a blower is driven, along with rotation of a rotor, vibration is generated in a stator. In the respective documents cited above, a stator of a motor is directly fixed to a casing. For that reason, in the structures of the respective documents cited above, the vibration generated in the stator is easily transferred to the casing. Thus, it is difficult to reduce vibration and noises generated during the operation of the blower.

In order to reduce the vibration of the blower, it is thinkable to interpose another member between the stator and the casing, thereby covering the periphery of the stator with another member. However, during the operation of the blower, the stator generates heat due to the power supply to coils. Although vibration can be reduced by merely covering the periphery of the stator with another member, it is difficult to dissipate the heat generated in the stator. That is to say, in the centrifugal blower, the compatibility of vibration resistance and heat dissipation is a problem that involves technical difficulties.

SUMMARY OF THE INVENTION

In accordance with an aspect of the present invention, there is provided a centrifugal blower, including: a casing; an impeller disposed within the casing; and a motor arranged to rotate the impeller about a center axis, wherein the casing includes an intake port opened toward a center of the impeller, an exhaust port positioned radially outward of the impeller and the motor, and a wind tunnel arranged to bring the intake port and the exhaust port into communication with each other and arranged to extend in a ring shape around the motor, the motor includes a rotor fixed to the impeller either directly or through another member, a stator disposed radially outward of the rotor and arranged to generate rotating magnetic fields between the stator and the rotor, and a stator housing arranged to hold the stator, and the stator housing includes a radial contact surface which makes contact with the casing in a radial direction, a circumferential contact surface which makes contact with the casing in a circumferential direction, an axial contact surface which makes contact with the casing in an axial direction, and a heat dissipating surface exposed to the wind tunnel.

According to one exemplary preferred embodiment of the present invention, the casing and the stator housing are brought into contact with each other in the radial direction, the circumferential direction and the axial direction. This makes it possible to increase the contact area between the casing and the stator housing, thereby reducing the vibration of the blower. In addition, it is possible to efficiently dissipate the heat generated in the stator from the heat dissipating surface of the stator housing to the gas existing within the wind tunnel.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Some exemplary preferred embodiments of the present invention will now be described with reference to the accompanying drawings. In the subject application, the direction parallel to or substantially parallel to a center axis of a motor provided within a blower will be referred to as an "axial direction". The direction orthogonal to or substantially orthogonal to the center axis of the motor will be referred to as a "radial direction". The direction extending along an arc centered at the center axis of the motor will be referred to as a "circumferential direction". In the preferred embodiments described below, the shape and positional relationship of the respective parts will be described by defining the axial direction as an up-down direction and by defining the side of an impeller with respect to a motor as an upper side. However, the definition of the up-down direction is not intended to limit the in-use direction of the blower according to the present invention.

Figure 1:
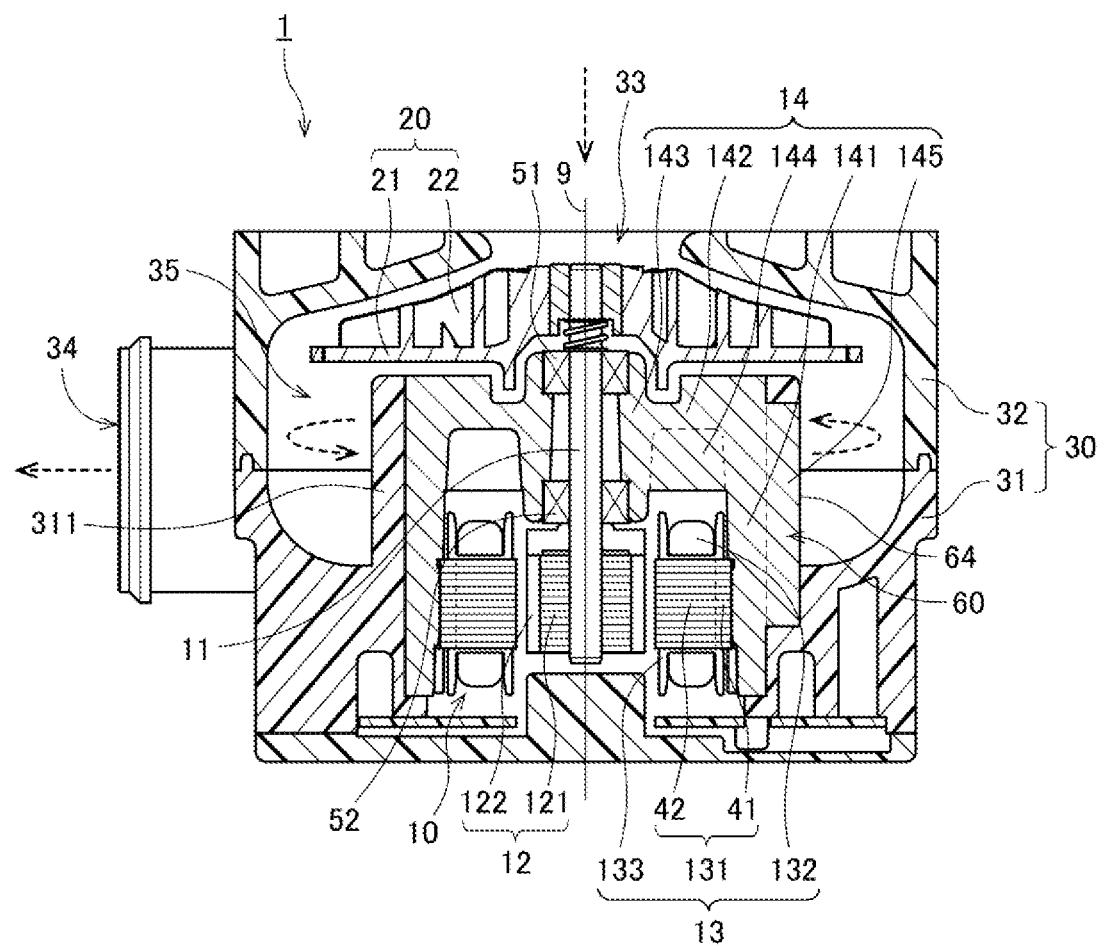
FIG. 1 is a vertical sectional view of a blower according to a first preferred embodiment.

FIG. 1 is a vertical sectional view of a blower 1 according to a first preferred embodiment of the present invention. The blower 1 is a so-called centrifugal blower which discharges an axially-sucked gas in a tangential direction by rotating an impeller 20 with the power of a motor 10. For example, the blower 1 is used to feed an air into a human respiratory tract during sleep. Specifically, the blower 1 is mounted to a medical-purpose artificial respirator for use in a nasal continuous positive airway pressure (CPAP) therapy by which an airway is secured during sleep of a patient who suffers from a sleep apnea syndrome. When a patient wears the artificial respirator and goes to bed, an air is continuously fed into the respiratory tract of the patient during sleep.

As illustrated in FIG. 1, the blower 1 of the present preferred embodiment preferably includes a motor 10, an impeller 20 and a casing 30.

The motor 10 is a drive power source for rotating the impeller 20. The motor 10 rotates the impeller 20 about a center axis 9. The motor 10 preferably includes a shaft 11, a rotor 12, a stator 13 and a stator housing 14. The shaft 11 is a columnar member disposed along the center axis 9. The impeller 20 is fixed to an upper end portion of the shaft 11. That is to say, in the present preferred embodiment, the rotor 12 and the impeller 20 are fixed to each other through the shaft 11. The impeller 20 is disposed within the casing 30.

The rotor 12 is fixed to the impeller 20 either directly or through another member. The rotor 12 preferably includes a cylindrical rotor core 121 and a magnet 122. For example, laminated steel plates as magnetic bodies are used as the rotor core 121. The magnet 122 is fixed to an outer circumferential surface of the rotor core 121. On the radial outer surface of the magnet 122, an N pole and an S pole are alternately magnetized in the circumferential direction. The magnet 122 may be composed of a plurality of magnets or a single annular magnet.

The stator 13 is disposed radially outward of the rotor 12. The stator 13 preferably includes a stator core 131 and a plurality of coils 132. For example, laminated steel plates as magnetic bodies are used as the stator core 131. The stator core 131 preferably includes a ring-shaped core-back 41 and a plurality of teeth 42 protruding radially inward from the core-back 41. The teeth 42 are disposed at a regular interval in the circumferential direction. The coils 132 are configured by conductive wires wound around the respective teeth 42. A resin-made insulator 133 is interposed between the teeth 42 and the coils 132. Thus, the teeth 42 and the coils 132 are electrically insulated from each other.

The stator 13 generates rotating magnetic fields between the stator 13 and the rotor 12. More specifically, if a drive current is supplied to the coils 132 of the stator 13, magnetic fluxes are generated in the teeth 42 of the stator core 131. A circumferential torque is generated by the action of the magnetic fluxes generated between the teeth 42 and the magnet 122. As a result, the rotor 12 and the shaft 11 are rotated about the center axis 9. As the shaft 11 rotates, the impeller 20 fixed to the shaft 11 is also rotated about the center axis 9. In other words, the shaft 11 rotates together with the rotor 12 and the impeller 20.

Figure 2:
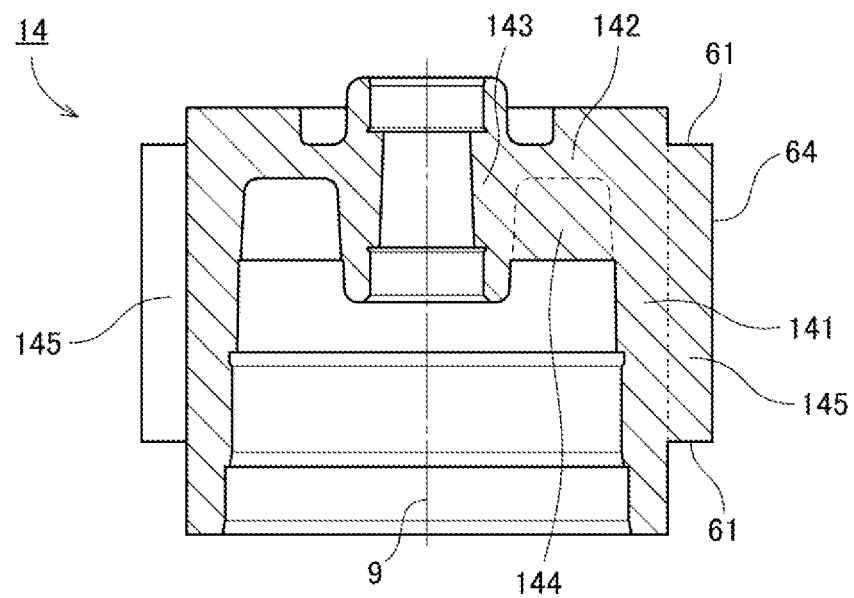
FIG. 2 is a vertical sectional view of a stator housing according to the first preferred embodiment.
Figure 3:
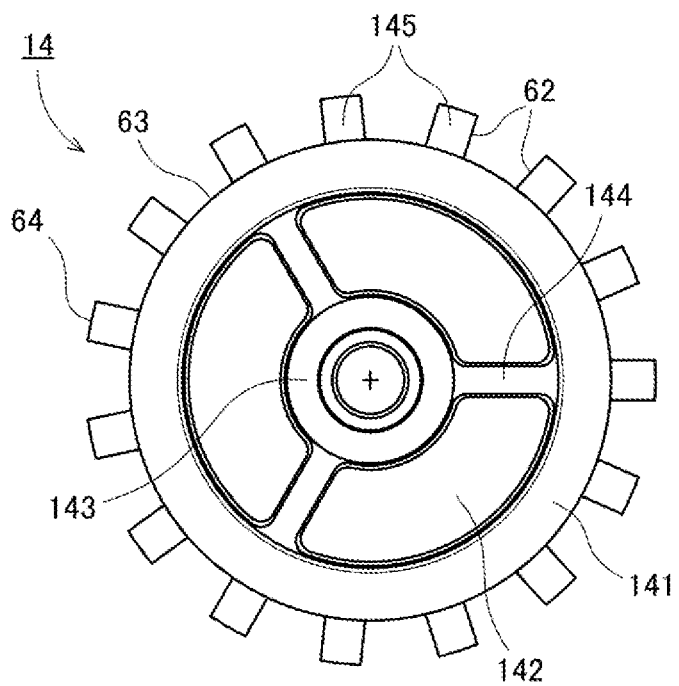
FIG. 3 is a bottom view of the stator housing according to the first preferred embodiment.

The stator housing 14 holds the stator 13. More specifically, the stator housing 14 is a member fixed to the casing 30 and arranged to hold the stator 13. FIG. 2 is a vertical sectional view of the stator housing 14. FIG. 3 is a bottom view of the stator housing 14. As illustrated in FIGS. 1 to 3, the stator housing 14 preferably includes a tubular portion 141, a disc portion 142, a bearing holding portion 143 and a plurality of ribs 144.

The tubular portion 141 is arranged radially outward of the stator 13 and is formed in a substantially cylindrical shape so as to extend in the axial direction. The stator core 131 is fixed to an inner circumferential surface of the tubular portion 141. The upper end portion of the tubular portion 141 extends upward beyond the stator 13. The disc portion 142 extends radially inward from the upper end portion of tubular portion 141. The bearing holding portion 143 extends upward and downward from the radial inner end portion of the disc portion 142 in a substantially cylindrical shape. The ribs 144 are disposed at the side of the lower surface of the disc portion 142 to radially interconnect an outer circumferential surface of the bearing holding portion 143 and the inner circumferential surface of the tubular portion 141. The rigidity of the stator housing 14 is enhanced by the ribs 144.

The stator housing 14 preferably includes a radial contact surface 63 which makes contact with the casing 30 in the radial direction, circumferential contact surfaces 62 which make contact with the casing 30 in the circumferential direction, axial contact surfaces 61 which make contact with the casing 30 in the axial direction, and heat dissipating surfaces 64 exposed to a wind tunnel 35. As will be described later, the stator housing 14 of the present preferred embodiment becomes a dissipation route of heat generated in the stator 13. For that reason, metal exhibiting high heat dissipation, such as aluminum, aluminum alloy or the like, may be used as a material of the stator housing 14. Particularly, in a medical instrument such as an artificial respirator or the like which is directly handled by a patient, the reliability and light weight of the medical instrument are important design subjects. Use of aluminum or aluminum alloy makes it possible to reduce the weight of the blower 1 while enhancing the strength of the stator housing 14.

A plurality of bearings is interposed between the stator housing 14 or another member fixed to the stator housing 14 and the shaft 11. In the present preferred embodiment, a pair of bearings 51 and 52 is interposed between the bearing holding portion 143 and the shaft 11. For example, ball bearings are used as the bearings 51 and 52. An outer race of each of the bearings 51 and 52 is fixed to an inner circumferential surface of the bearing holding portion 143. An inner race of each of the bearings 51 and 52 is fixed to an outer circumferential surface of the shaft 11. Thus, the shaft 11, the rotor 12 and the impeller 20 are rotatably supported with respect to the stator housing 14.

The bearings 51 and 52 are disposed at the same side of the rotor 12 in the axial direction. In the present preferred embodiment, all the bearings 51 and 52 are disposed axially upward of the rotor 12 at the side of the impeller 20. All the bearings 51 and 52 are held by the stator housing 14. If the two bearings 51 and 52 are disposed at the same side of the rotor 12 in the axial direction as mentioned above, it becomes easy to hold the two bearings 51 and 52 with a single part. Furthermore, if the bearings 51 and 52 are held by a single part, it is easy to dispose the shaft 11 in a coaxial relationship with the center axis 9.

In the present preferred embodiment, the bearings 51 and 52 do not completely protrude upward from the disc portion 142 of the stator housing 14. The upper bearing 51 is disposed in such a position as to radially overlap with a portion of the disc portion 142 of the stator housing 14. The lower bearing 52 is disposed in such a position as to radially overlap with the tubular portion 141 of the stator housing 14. By doing so, the distance from the bearings 51 and 52 to the tubular portion 141 becomes short. Accordingly, it is possible to suppress tilting of the stator housing 14 with respect to the shaft 11.

The impeller 20 is disposed at the upper side of the stator housing 14 and is fixed to the shaft 11. The impeller 20 preferably includes a substantially disc-shaped blade support portion 21 and a plurality of blades 22. The blade support portion 21 extends perpendicularly or substantially perpendicularly with respect to the center axis 9. The blades 22 are disposed at a regular interval in the circumferential direction. Furthermore, the blades 22 extend radially along an upper surface of the blade support portion 21. For example, a resin such as PBT (polybutylene terephthalate), PC (polycarbonate) or the like may be used as a material of the impeller 20. However, a material other than a resin, such as metal or the like, may be used as the material of the impeller 20.

The motor 10 and the impeller 20 are disposed within the casing 30. As illustrated in FIG. 1, the casing 30 of the present preferred embodiment preferably includes a first casing member 31 and a second casing member 32 disposed above the first casing member 31. The first casing member 31 surrounds the stator 13 and the stator housing 14. The second casing member 32 surrounds the impeller 20.

The first casing member 31 and the second casing member 32 are fixed to each other by screwing or engagement. An elastomer-made seal material (not illustrated) is interposed between the first casing member 31 and the second casing member 32. Leakage of a gas from a gap between the first casing member and the second casing member 32 is prevented by the seal member.

For example, a resin such as PBT (polybutylene terephthalate), PC (polycarbonate) or the like may be used as a material of the first casing member 31 and the second casing member 32. The first casing member 31 is obtained by so-called insert molding in which the stator housing 14 is disposed within a mold and a resin is introduced into and solidified within the mold. That is to say, the first casing member 31 (the casing 30) of the present preferred embodiment is a resin-molded article which uses the stator housing 14 as an insert part. Use of the insert molding makes it possible to bring the stator housing 14 and the first casing member 31 into close contact with each other.

Alternatively, the first casing member 31 may be molded independently of the stator housing 14. The stator housing 14 may be fixed to the molded first casing member 31 by an adhesive agent or the like.

The casing 30 preferably includes an intake port 33, an exhaust port 34 and a wind tunnel 35. At the upper side of the impeller 20, the intake port 33 axially penetrates the second casing member 32. That is to say, the intake port 33 is opened toward the center of the impeller 20. More specifically, the intake port 33 is opened from a space existing above the second casing member 32 toward the center of the impeller 20. The exhaust port 34 is positioned radially outward of the impeller 20 and the motor 10. At the radial outer side of the motor 10 and the impeller 20, the exhaust port 34 is opened in a tangential direction of an imaginary circle centered at the center axis 9. Furthermore, the wind tunnel 35 serving as a flow path of a gas is defined within the casing 30. The wind tunnel 35 extends in a ring shape around the motor 10 and the impeller 20. In addition, the intake port 33 and the exhaust port 34 communicate with each other through the wind tunnel 35. In other words, the wind tunnel 35 brings the intake port 33 and the exhaust port 34 into communication with each other and extends in a ring shape around the motor 10.

During the operation of the motor 10, the impeller 20 rotates together with the shaft 11. Thus, a gas is sucked from a space above the casing 30 into the casing 30 through the intake port 33. The sucked gas is accelerated by the impeller 20 so as to swirl within the wind tunnel 35. The gas swirling within the wind tunnel 35 is discharged to the outside of the casing 30 through the exhaust port 34.

Next, descriptions will be made on the detailed shape of the stator housing 14 and the first casing member 31.

As illustrated in FIGS. 1, 2 and 3, a plurality of gear-shaped salient portions 145 is provided on the outer circumferential surface of the stator housing 14 of the present preferred embodiment. Each of the salient portions 145 protrude radially outward from the outer circumferential surface of the tubular portion 141. The salient portions 145 are disposed at a substantially regular interval in the circumferential direction. Each of the salient portions 145 extends in the axial direction on the outer circumferential surface of the stator housing 14. More specifically, each of the salient portions 145 axially extends in a substantially rectangular parallelepiped shape on the outer circumferential surface of the stator housing 14.

In the meantime, the casing 30 preferably includes a ring-shaped holder portion 311 positioned radially inward of the wind tunnel 35. More specifically, the first casing member 31 preferably includes a holder portion 311 formed around the stator housing 14. The holder portion 311 is positioned radially inward of the wind tunnel 35. The holder portion 311 extends upward along the outer circumferential surface of the tubular portion 141 between the salient portions 145 and has an upper end portion extending in a ring shape. The holder portion 311 of the present preferred embodiment includes a plurality of radially-penetrating through-holes 60 or a plurality of radially-penetrating cutouts. The through-holes 60 are disposed at a substantially regular interval in the circumferential direction. The salient portions 145 of the stator housing 14 are respectively fitted to the through-holes 60 or the cutouts. That is to say, the salient portions 145 of the stator housing 14 of the present preferred embodiment are respectively fitted to the through-holes 60 of the holder portion 311. The outer end surfaces of the salient portions 145 become heat dissipating surfaces 64.

Thus, in the present preferred embodiment, the upper and lower surfaces of the salient portions 145 of the stator housing 14 become axial contact surfaces 61 that make contact with the holder portion 311 of the first casing member 31 in the axial direction. The circumferential opposite end surfaces of each of the salient portions 145 become circumferential contact surfaces 62 that make contact with the holder portion 311 of the first casing member 31 in the circumferential direction. The outer circumferential surface of the tubular portion 141 becomes a radial contact surface 63 that makes contact with the holder portion 311 of the first casing member 31 in the radial direction.

As described above, in the blower 1 of the present preferred embodiment, the stator housing 14 and the first casing member 31 make surface-to-surface contact with each other in three directions, namely the radial direction, the circumferential direction and the axial direction. As a result, the contact area between the stator housing 14 and the first casing member 31 becomes larger. Accordingly, the stator housing and the first casing member 31 are strongly fixed to each other. During the operation of the blower 1, the vibration generated in the stator 13 is transferred to the first casing member 31 through the stator housing 14. Since the stator housing 14 is held in three directions with respect to the first casing member 31, it is possible to efficiently suppress the vibration thus transferred. Accordingly, it is possible to reduce the vibration and noises generated during the operation of the blower 1.

The holder portion 311 of the first casing member 31 does not cover radial outer end surfaces of the salient portions 145. For that reason, the radial outer end surfaces of the salient portions 145 are exposed to the wind tunnel 35. During the operation of the blower 1, the heat generated in the coils 132 is transferred to the stator housing 14 via the stator core 131. Then, the heat is dissipated from the radial outer end surfaces of the salient portions 145 to the gas existing within the wind tunnel 35. Thus, the stator 13 is efficiently cooled. As described above, in the present preferred embodiment, the radial outer end surfaces of the salient portions 145 become the heat dissipating surfaces 64 that dissipate the heat of the stator 13 to the outside.

Particularly, in the present preferred embodiment, the salient portions 145 are disposed at a substantially regular interval in the circumferential direction. For that reason, it is possible to uniformly obtain the effects of vibration reduction and heat dissipation around the stator 13.

In the present preferred embodiment, the radial outer surface of the holder portion 311 and the radial outer end surfaces of the salient portions 145 are positioned on an identical imaginary cylindrical plane centered at the center axis 9. The identical imaginary cylindrical plane includes a substantially identical imaginary cylindrical plane. For that reason, as compared with a case where the radial outer end surfaces of the salient portions 145 are positioned radially inward of the radial outer surface of the holder portion 311, it is easy for the gas existing within the wind tunnel 35 to make contact with the end surfaces of the salient portions 145. Accordingly, the heat of the salient portions 145 is efficiently transferred to the gas existing within the wind tunnel 35. That is to say, in the present preferred embodiment, it is possible to efficiently dissipate heat from the salient portions 145 to the gas existing within the wind tunnel 35.

However, the salient portions 145 of the present preferred embodiment do not protrude from the holder portion 311 into the wind tunnel 35. For that reason, the flow of the gas existing within the wind tunnel 35 is not hindered by the salient portions 145. Accordingly, in the present preferred embodiment, it is possible to prevent loss of an air volume otherwise caused by the salient portions 145 and to prevent generation of wind noises.

In the present preferred embodiment, the material of the stator housing 14 is metal and the material of the first casing member 31 is a resin. That is to say, the material of the stator housing 14 and the material of the casing 30 (the first casing member 31) differ from each other. If different materials are brought into contact with each other in this way, it is possible to efficiently attenuate the vibration transferred from the stator housing 14 to the first casing member 31. Furthermore, resonance is unlikely to occur between the stator housing 14 and the first casing member 31. Accordingly, it is possible to efficiently reduce the vibration and noises generated during the operation of the blower 1.

Particularly, in an artificial respirator used by a patient during sleep, quietness and long-term reliability are important. If the structure of the present preferred embodiment is employed, it is possible to reduce the vibration and noises generated during the operation of the blower 1. Furthermore, it is possible to efficiently dissipate heat of the stator 13 to the outside, thereby improving the service life of the blower 1.

In the present preferred embodiment, the through-holes 60 as closed holes are provided in the holder portion 311 of the first casing member 31. Alternatively, the holder portion 311 may include a plurality of cutouts opened upward or downward, instead of the through-holes 60. The salient portions 145 of the stator housing 14 may be fitted to the cutouts. In addition, the salient portions 145 do not necessarily need to be disposed at a regular interval in the circumferential direction. As an alternative example, the salient portions 145 may be disposed at irregular intervals in the circumferential direction.

Figure 4:
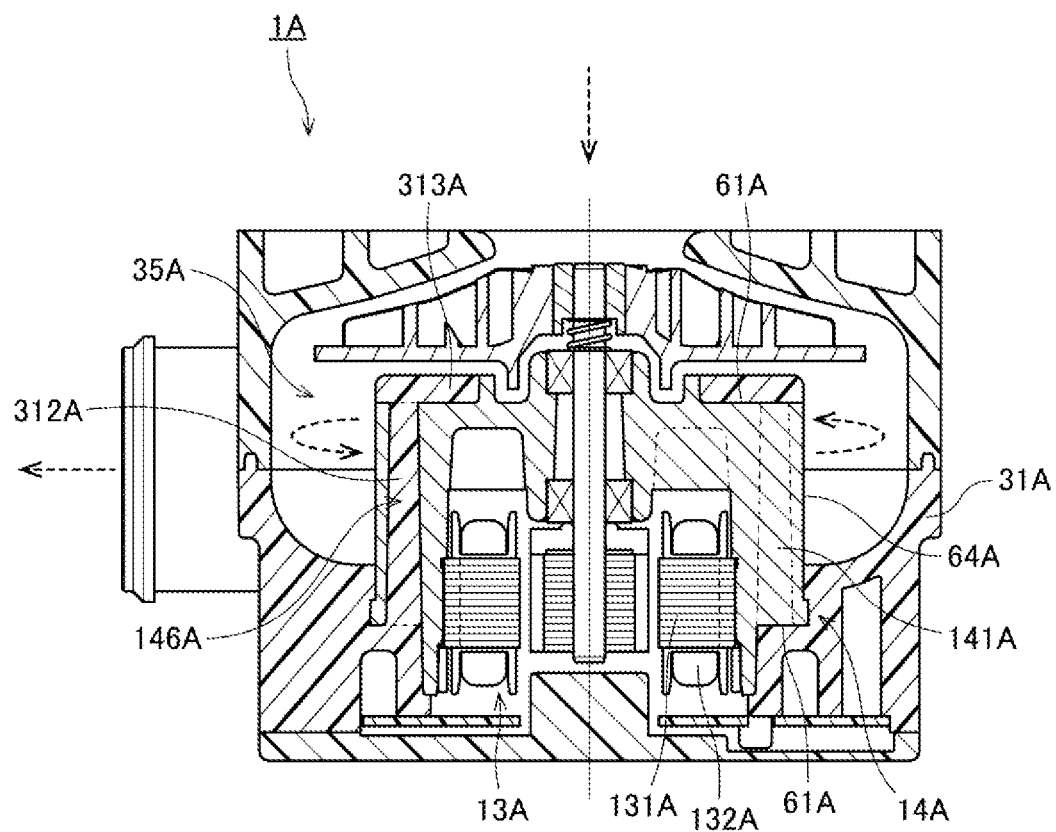
FIG. 4 is a vertical sectional view of a blower according to a second preferred embodiment.
Figure 5:
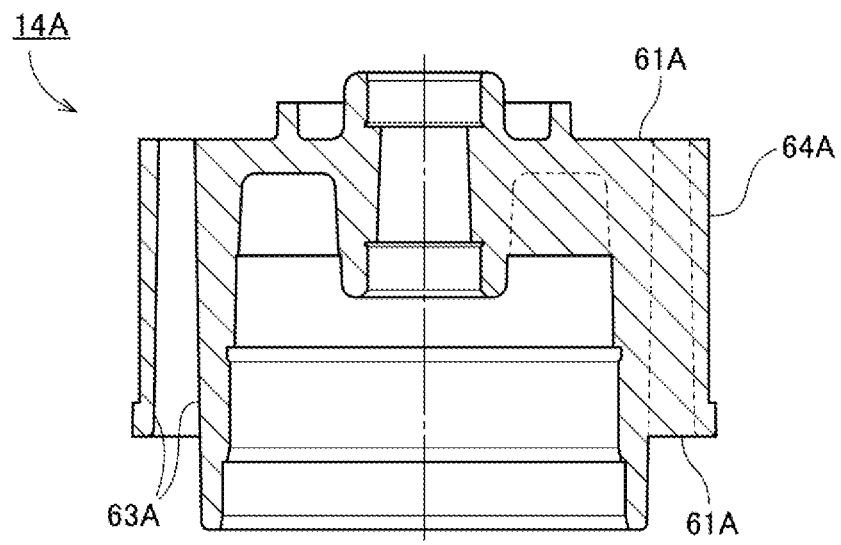
FIG. 5 is a vertical sectional view of a stator housing according to the second preferred embodiment.
Figure 6:
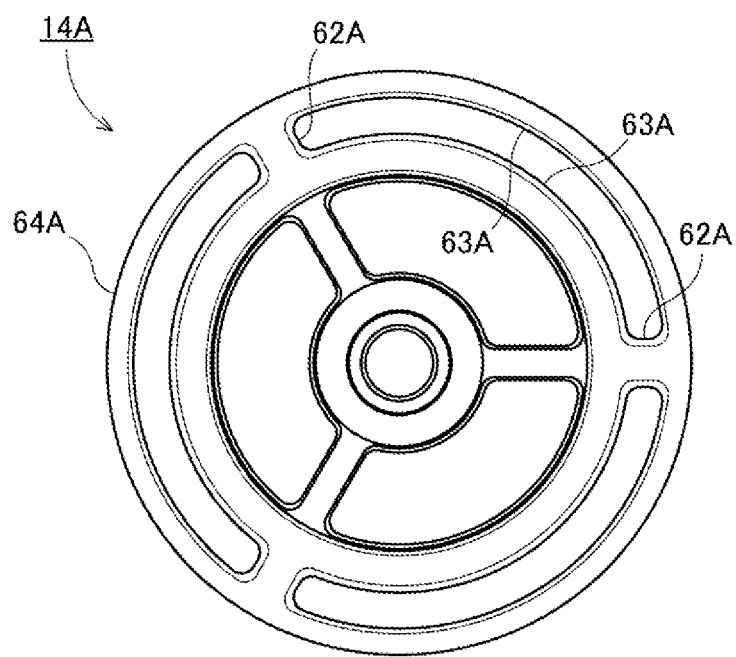
FIG. 6 is a bottom view of the stator housing according to the second preferred embodiment.

Subsequently, descriptions will be made on a second preferred embodiment of the present invention. FIG. 4 is a vertical sectional view of a blower 1A according to a second preferred embodiment. FIG. 5 is a vertical sectional view of a stator housing 14A according to the second preferred embodiment. FIG. 6 is a bottom view of the stator housing 14A according to the second preferred embodiment. The blower 1A of the present preferred embodiment differs from the blower 1 of the first preferred embodiment in terms of the structures of a stator housing 14A and a first casing member 31A. Thus, the following descriptions will be centered on the structures of the stator housing 14A and the first casing member 31A. Other parts remain the same as those of the first preferred embodiment and, therefore, duplicate descriptions thereon will be omitted.

As illustrated in FIGS. 4, 5 and 6, the stator housing 14A of the present preferred embodiment preferably includes a substantially cylindrical outer circumferential surface having no unevenness. The outer circumferential surface of the stator housing 14A is exposed to the wind tunnel 35A. During the operation of the blower 1A, the heat generated in the coils 132A is transferred to the stator housing 14A via the stator core 131A. Then, the heat of the stator housing 14A is transferred from the outer circumferential surface of the stator housing 14A to the gas existing within the wind tunnel 35A. Thus, the stator 13A is cooled. As described above, in the present preferred embodiment, the cylindrical outer circumferential surface of the stator housing 14A becomes a heat dissipating surface 64A that dissipates the heat of the stator 13A to the outside.

The stator housing 14A of the present preferred embodiment preferably includes three through-holes 146A. Each of the through-holes 146A axially penetrates the tubular portion 141A of the stator housing 14A. In the meantime, the first casing member 31A preferably includes three columnar portions 312A and a ring-shaped portion 313A. The three columnar portions 312A axially extend within the through-holes 146A of the stator housing 14A. The ring-shaped portion 313A is an annular portion that covers the upper surface of the tubular portion 141A.

The first casing member 31A is manufactured by introducing a resin into a mold and solidifying the resin in a state in which the stator housing 14A is disposed within the mold. At this time, the resin is also filled in the three through-holes 146A of the stator housing 14A. Thus, the three columnar portions 312A are formed.

In the present preferred embodiment, the upper and lower surfaces of the stator housing 14A become axial contact surfaces 61A that make contact with the first casing member 31A in the axial direction. The surfaces which define each of the through-holes 146A of the stator housing 14A preferably include circumferential contact surfaces 62A that make contact with each of the columnar portions 312A of the first casing member 31A in the circumferential direction and radial contact surfaces 63A that make contact with each of the columnar portions 312A of the first casing member 31A in the radial direction.

As described above, even in the blower 1A of the present preferred embodiment, the stator housing 14A and the first casing member 31A make surface-to-surface contact with each other in three directions, namely the radial direction, the circumferential direction and the axial direction. Thus, the contact area between the stator housing 14A and the first casing member 31A increases. Accordingly, the stator housing 14A and the first casing member 31A are strongly fixed to each other. During the operation of the blower 1A, the vibration generated in the stator 13A is transferred to the first casing member 31A through the stator housing 14A. Since the stator housing 14A is held in three directions with respect to the first casing member 31A, it is possible to efficiently suppress the vibration thus transferred. Accordingly, it is possible to reduce the vibration and noises generated during the operation of the blower 1A.

In the blower 1A of the present preferred embodiment, the outer circumferential surface of the stator housing 14A is exposed to the wind tunnel 35A over the entire circumference thereof. In other words, the heat dissipating surface 64A is a cylindrical surface exposed to the wind tunnel 35A over the entire circumference thereof. For that reason, in the present preferred embodiment, it is possible to obtain a heat dissipating effect over the entire circumference of the motor 10A.

While some exemplary preferred embodiments of the present invention have been described above, the present invention is not limited to the aforementioned preferred embodiments.

Figure 7:
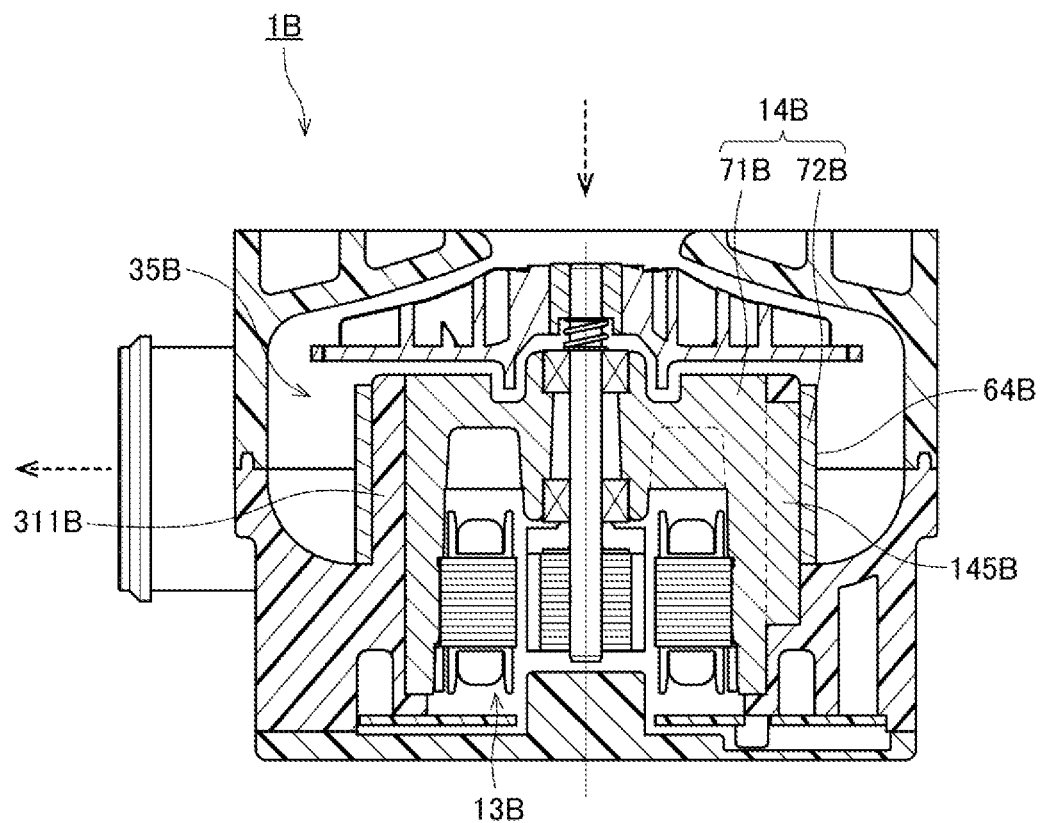
FIG. 7 is a vertical sectional view of a blower according to a modification.

FIG. 7 is a vertical sectional view of a blower 1B according to one modification. In the modification illustrated in FIG. 7, the stator housing 14B preferably includes two members, namely a housing body 71B and a ring member 72B. The housing body 71B has a shape equivalent to the shape of the stator housing 14 of the first preferred embodiment. The ring member 72B is a cylindrical member and is attached to the radial outer side of the housing body 71B and the holder portion 311B. In other words, the ring member 72B is positioned radially outward of the housing body 71B. A fixing method of the ring member 72B may be either press-fit or bonding using an adhesive agent. As a material of the ring member 72B, it may be possible to use, e.g., metal having high heat conductivity such as aluminum or the like. The housing body 71B and the ring member 72B make contact with each other. Specifically, the inner circumferential surface of the ring member 72B makes contact with the radial outer end surfaces of a plurality of salient portions 145B.

By doing so, the heat transferred from the stator 13B to the housing body 71B is transferred to a gas existing within the wind tunnel 35B via the ring member 72B. At least the outer circumferential surface of the ring member 72B is a heat dissipating surface 64B. That is to say, in the modification illustrated in FIG. 7, the entirety of the cylindrical outer circumferential surface of the ring member 72B becomes a heat dissipating surface 64B that dissipates heat of the stator 13B to the outside. Accordingly, as compared with the first preferred embodiment, the ring member 72B can increase the area of the heat dissipating surface 64B. As a result, the ring member 72B can further enhance the heat dissipation effect.

Figure 8:
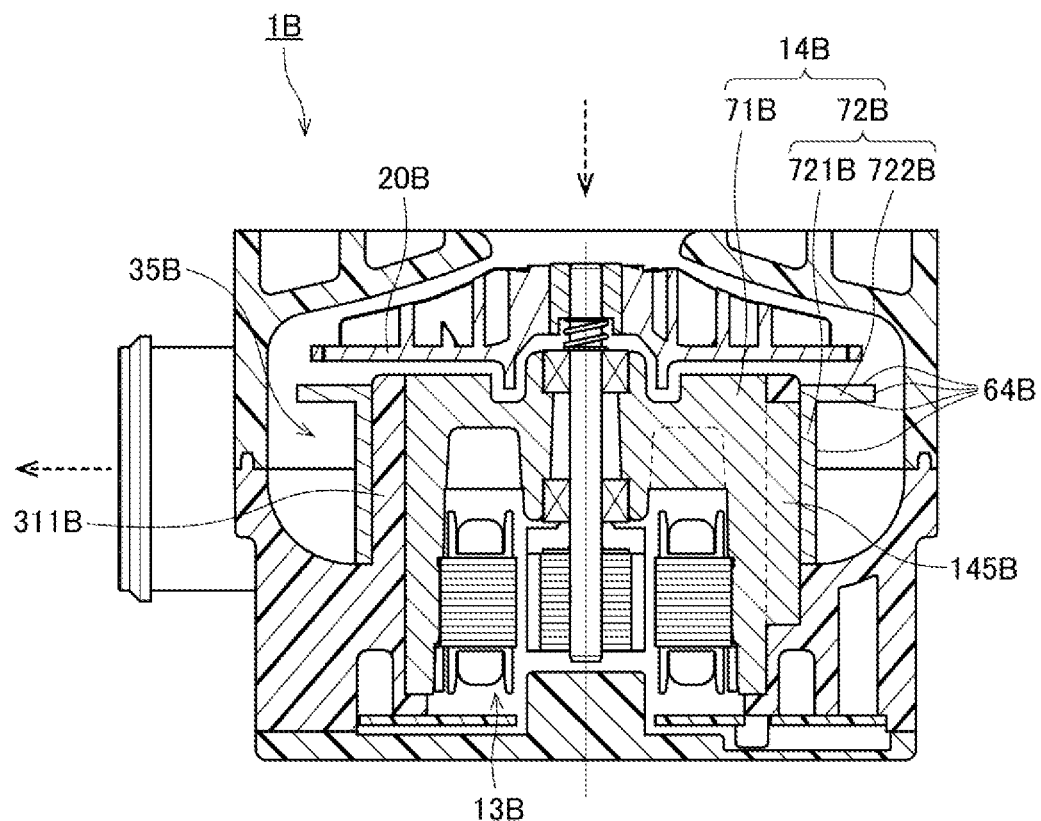
FIG. 8 is a vertical sectional view of a blower according to another modification.

The shape of the ring member 72B having the structure of FIG. 7 may be modified to a shape illustrated in FIG. 8. In the modification of FIG. 8, the ring member 72B preferably includes a cylindrical portion 721B and a flange portion 722B. The cylindrical portion 721B is positioned radially outward of the housing body 71B and the holder portion 311B so as to axially extend in a cylindrical shape. The flange portion 722B protrudes radially outward from the cylindrical portion 721B. More specifically, the flange portion 722B protrudes radially outward from the upper end of the cylindrical portion 721B. In the modification of FIG. 8, the outer circumferential surface of the cylindrical portion 721B and the surface of the flange portion 722B become heat dissipating surfaces 64B. Accordingly, as compared with the modification of FIG. 7, it is possible to further increase the area of the heat dissipating surfaces 64B. As a result, it is possible to further enhance the heat dissipation effect.

In the modification of FIG. 8, the radial outer end of the flange portion 722B is positioned radially outward of the radial outer end of the impeller 20B. By doing so, it is possible to restrain an airflow, which comes into a space existing below the flange portion 722B, from colliding with a subsequent airflow introduced from the impeller 20B into the wind tunnel 35B. This makes it possible to further reduce noises generated during the operation of the blower 1B.

Figure 9:
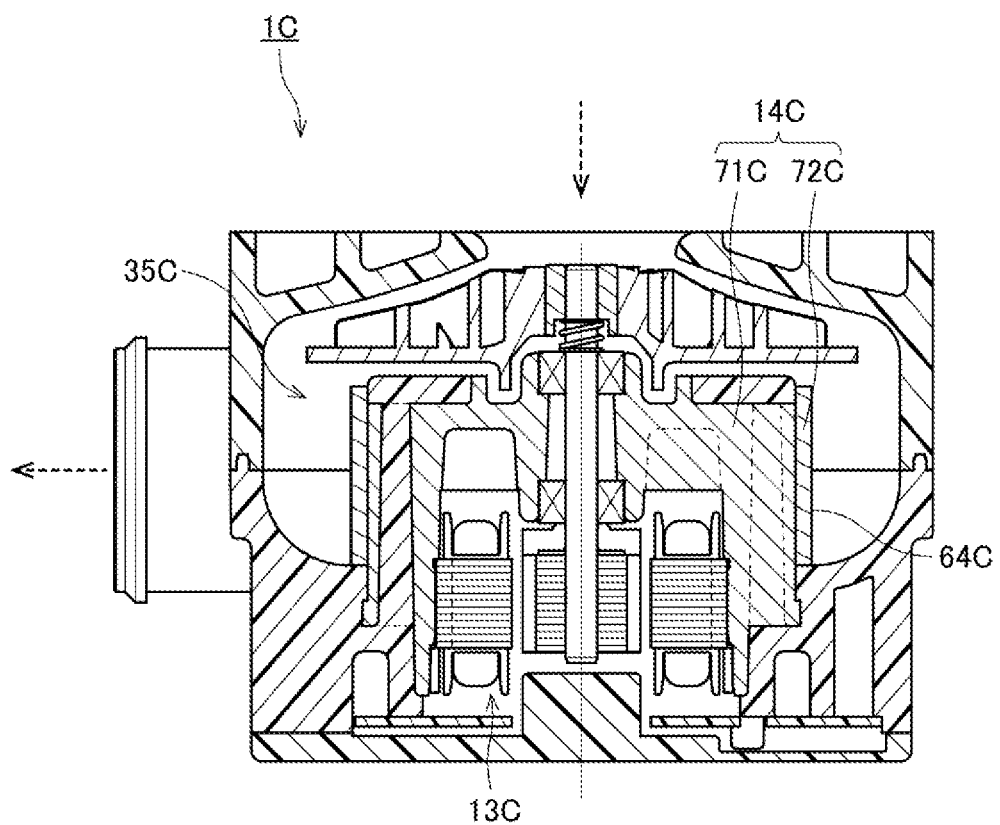
FIG. 9 is a vertical sectional view of a blower according to a further modification.

FIG. 9 is a vertical sectional view of a blower 1C according to a further modification. In the modification of FIG. 9, the stator housing 14C preferably includes two members, namely a housing body 71C and a ring member 72C. The housing body 71C has a shape equivalent to the shape of the stator housing 14A of the second preferred embodiment. The ring member 72C is a cylindrical member and is attached to the radial outer side of the housing body 71C. A fixing method of the ring member 72C may be either press-fit or bonding using an adhesive agent. As a material of the ring member 72C, it may be possible to use, e.g., metal having high heat conductivity such as aluminum or the like. The inner circumferential surface of the ring member 72C makes contact with the cylindrical outer circumferential surface of the housing body 71C.

By doing so, the heat transferred from the stator 13C to the housing body 71C can be dissipated to a gas existing within the wind tunnel 35C via the ring member 72C. That is to say, in the modification illustrated in FIG. 9, the entirety of the cylindrical outer circumferential surface of the ring member 72C becomes a heat dissipating surface 64C that dissipates heat of the stator 13C to the outside. Particularly, in the modification of FIG. 9, the diameter of the outer circumferential surface of the ring member 72C is larger than the diameter of the housing body 71C, and the axial length of the outer circumferential surface of the ring member 72C is larger than the axial length of the outer circumferential surface of the housing body 71C. Accordingly, as compared with the second preferred embodiment, it is possible to increase the area of the heat dissipating surface 64C. As a result, it is possible to further enhance the heat dissipation effect.

Figure 10:
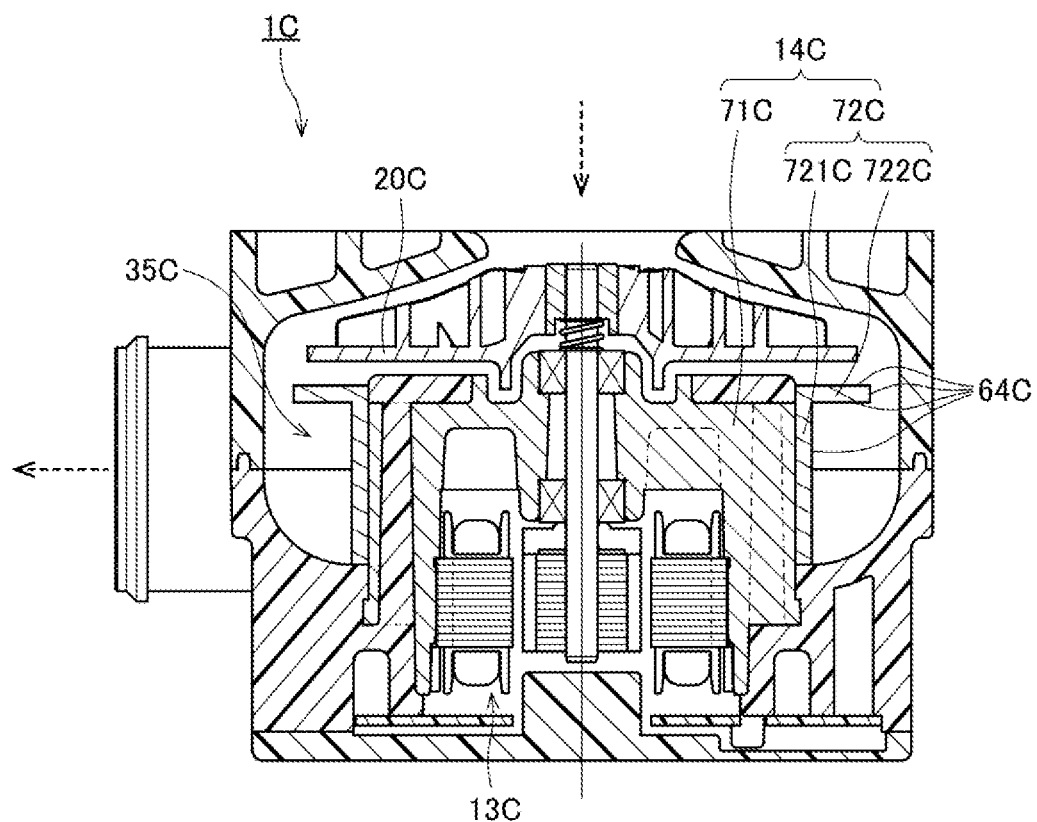
FIG. 10 is a vertical sectional view of a blower according to a still further modification.

The shape of the ring member 72C having the structure of FIG. 9 may be modified to a shape illustrated in FIG. 10. In the modification of FIG. 10, the ring member 72C preferably includes a cylindrical portion 721C and a flange portion 722C. The cylindrical portion 721C is positioned radially outward of the housing body 71C so as to axially extend in a cylindrical shape. The flange portion 722C protrudes radially outward from the upper end of the cylindrical portion 721C. In the modification of FIG. 10, the outer circumferential surface of the cylindrical portion 721C and the surface of the flange portion 722C become heat dissipating surfaces 64C. Accordingly, as compared with the modification of FIG. 9, it is possible to further increase the area of the heat dissipating surfaces 64C. As a result, it is possible to further enhance the heat dissipation effect.

In the modification of FIG. 10, the radial outer end of the flange portion 722C is positioned radially outward of the radial outer end of the impeller 20C. By doing so, it is possible to restrain an airflow, which comes into a space existing below the flange portion 722C, from colliding with a subsequent airflow introduced from the impeller 20C into the wind tunnel 35C. Thus, in the modification of FIG. 10, it is possible to further reduce noises generated during the operation of the blower 10.

In the preferred embodiments described above, the rotor and the impeller are fixed to each other through the shaft. However, the rotor and the impeller may be directly fixed to each other without going through the shaft.

Furthermore, in the preferred embodiments described above, a pair of bearings is interposed between the stator housing and the shaft. Alternatively, another member may be fixed to the radial inner side of the stator housing, and a plurality of bearings may be interposed between another member and the shaft. In the preferred embodiments described above, a plurality of bearings is disposed at the same side of the rotor in the axial direction. Alternatively, a plurality of bearings may be divisionally disposed at the upper and lower sides of the rotor. In addition, the number of bearings may be three or more.

The blower of each of the aforementioned preferred embodiments is mounted to a medical-purpose artificial respirator. However, the blower of the present invention may be used in applications other than a medical instrument, such as a cooling fan, a cleaner and the like.

The detailed shapes of the respective members constituting the blower may differ from the shapes illustrated in the drawings of the subject application. The respective elements appearing in the preferred embodiments and the modifications described above may be suitably combined unless a conflict arises.

The present invention may be used in, e.g., a centrifugal blower.

Features of the above-described preferred embodiments and the modifications thereof may be combined appropriately as long as no conflict arises.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A centrifugal blower, comprising:
   a casing;
   an impeller disposed within the casing; and
   a motor arranged to rotate the impeller about a center axis, wherein the casing includes an intake port opened toward a center of the impeller, an exhaust port positioned radially outward of the impeller and the motor, and a wind tunnel arranged to bring the intake port and the exhaust port into communication with each other and arranged to extend in a ring shape around the motor,
   the motor includes a shaft disposed along the center axis, a rotor fixed to the impeller through the shaft, a stator disposed radially outward of the rotor and arranged to generate rotating magnetic fields between the stator and the rotor, and a stator housing arranged to hold the stator,
   the stator housing includes a heat dissipating surface exposed to the wind tunnel, and at least one of a through-holes axially penetrated in a tubular portion of the stator housing, and,
   the heat dissipating surface includes a cylindrical surface exposed to the wind tunnel over an entire circumference, and
   surfaces which define each of the through-holes of the stator housing include circumferential contact surfaces and radial contact surfaces, wherein
   at least one of the circumferential contact surfaces and the radial contact surfaces make contact with a columnar portion of the casing.

2. The blower of claim 1, wherein the stator housing includes an axial contact surface that makes contact with the casing in the axial direction.

3. The blower of claim 1, wherein the casing includes a ring-shaped portion, columnar portions axially extend within the through-holes of the stator housing, and the ring-shaped portion is an annular portion that covers an upper surface of the tubular portion.

4. The blower of claim 1, wherein a material of the stator housing and a material of the casing differ from each other.

5. The blower of claim 1, wherein the material of the stator housing is metal, and the material of the casing is a resin.

6. The blower of claim 5, wherein the material of the stator housing is aluminum or an aluminum alloy.

7. The blower of claim 5, wherein the casing is a resin-molded article that uses the stator housing as an insert part.

8. The blower of claim 1, wherein the stator housing includes a housing body and a ring member positioned radially outward of the housing body,
   the housing body and the ring member are arranged to make contact with each other, and
   at least an outer circumferential surface of the ring member becomes the heat dissipating surface.

9. The blower of claim 8, wherein the ring member includes a cylindrical portion disposed radially outward of the housing body so as to axially extend in a cylindrical shape and a flange portion protruding radially outward from the cylindrical portion.

10. The blower of claim 1, further comprising:
    a plurality of bearings interposed between the stator housing and the shaft, wherein
    the bearings are disposed at the same side of the rotor in the axial direction.

11. The blower of claim 1, which is configured to be used to feed air to a respiratory tract of a sleeping human.

* * * * *